US012590931B2

(12) United States Patent
Ito et al.

(10) Patent No.: US 12,590,931 B2
(45) Date of Patent: Mar. 31, 2026

(54) CHARACTERISTICS MEASUREMENT DEVICE FOR OBJECT TO BE MEASURED AND CHARACTERISTICS MEASUREMENT METHOD FOR OBJECT TO BE MEASURED

(71) Applicant: JAPAN SCIENCE AND TECHNOLOGY AGENCY, Saitama (JP)

(72) Inventors: Kazuma Ito, Tokyo (JP); Nobuo Niimi, Tokyo (JP); Kenji Ikushima, Tokyo (JP)

(73) Assignee: JAPAN SCIENCE AND TECHNOLOGY AGENCY, Saitama (JP)

( * ) Notice: Subject to any disclaimer, the term of this patent is extended or adjusted under 35 U.S.C. 154(b) by 122 days.

(21) Appl. No.: 18/435,929

(22) Filed: Feb. 7, 2024

(65) Prior Publication Data

US 2024/0210458 A1     Jun. 27, 2024

Related U.S. Application Data

(63) Continuation-in-part of application No. PCT/JP2022/020793, filed on May 19, 2022.

(30) Foreign Application Priority Data

Aug. 25, 2021   (JP) ................................. 2021-137182

(51) Int. Cl.
*G01N 29/50*       (2006.01)
*A61B 5/00*        (2006.01)
(Continued)

(52) U.S. Cl.
CPC ........... *G01N 29/50* (2013.01); *G01N 29/343* (2013.01); *G01N 29/4436* (2013.01); *A61B 5/0093* (2013.01); *A61B 5/05* (2013.01)

(58) Field of Classification Search
CPC ....... A61B 5/0093; A61B 5/05; A61B 5/7203; G01N 29/036; G01N 29/04; G01N 29/24;
(Continued)

(56) References Cited

U.S. PATENT DOCUMENTS 6,009,755 A * 1/2000 Manome ............ G01N 29/0645
73/628
9,020,576 B2 * 4/2015 Nagatani .................. A61B 5/24
600/407

(Continued)

FOREIGN PATENT DOCUMENTS

JP      H09127254 A    5/1997
JP      2000221170 A   8/2000
(Continued)

OTHER PUBLICATIONS

Machine Translation of JP 2021-76474 (Year: 2021).*

(Continued)

*Primary Examiner* — Steven L Yeninas
(74) *Attorney, Agent, or Firm* — MUNCY, GEISSLER, OLDS & LOWE, P.C.

(57)             ABSTRACT

A characteristics measurement device for an object according to the invention comprises a sound wave generator that emits a sound wave; a receiver that receives from the object an electromagnetic field generated by the sound wave being irradiated to the object; a sound wave medium between the sound wave generator and the object the electromagnetic field separated from a reverberating electromagnetic field caused by reverberating vibrations of the sound wave generator in time; an inverse diffuse that inversely diffuses the electromagnetic field received by the receiver using a reference signal associated with the sound wave; and a measurement unit that extracts at least one characteristic selected from a group consisting of electrical characteristics, magnetic characteristics, electromechanical characteristics and
(Continued)

magnetomechanical characteristics of the object based on at least one measurement selected from a group consisting of intensity, phase and frequency of the inversely diffused electromagnetic field.

9 Claims, 14 Drawing Sheets

(51) Int. Cl.
| | |
|---|---|
| *A61B 5/05* | (2021.01) |
| *G01N 29/34* | (2006.01) |
| *G01N 29/44* | (2006.01) |

(58) Field of Classification Search
CPC .. G01N 29/2412; G01N 29/28; G01N 29/343; G01N 29/348; G01N 29/4436; G01N 29/50; G01N 27/72; G01N 27/725
See application file for complete search history.

(56) References Cited

U.S. PATENT DOCUMENTS

| | | | | |
|---|---|---|---|---|
| 2003/0141036 A1* | 7/2003 | Iizuka | ................... | G01N 29/50 |
| | | | | 164/413 |
| 2011/0056298 A1* | 3/2011 | O'keefe | ................ | G01N 29/04 |
| | | | | 73/622 |

| | | | | |
|---|---|---|---|---|
| 2011/0303014 A1* | 12/2011 | Kajitani | ............. | G01N 29/4454 |
| | | | | 73/632 |
| 2016/0143541 A1* | 5/2016 | He | ......................... | A61B 5/374 |
| | | | | 600/407 |
| 2022/0287618 A1* | 9/2022 | Ikushima | ............... | G01R 33/02 |

FOREIGN PATENT DOCUMENTS

| | | | |
|---|---|---|---|
| JP | 4919967 B2 | | 4/2012 |
| JP | 5892623 B2 | | 3/2016 |
| JP | 2020121120 A | | 8/2020 |
| JP | 2021076474 A | | 5/2021 |
| WO | WO-2007/05557 A2 | | 1/2007 |
| WO | WO-2007055057 A1 | | 5/2007 |
| WO | WO-2013011869 A1 | | 1/2013 |

OTHER PUBLICATIONS

Beaurepaire et al., "Coherent terahertz emission from ferromagnetic films excited by femtosecond laser pulses," Applied Physics Letters, vol. 84, No. 11, May 3, 2004, 4 pages.
International Search Report of PCT/JP2022/020793 and English translation, Jul. 12, 2022, 4 pages.
International Preliminary Report on Patentabliity of PCT/JP2022/020793 and English translation, Feb. 27, 2024, 10 pages.
Office Action issued for corresponding Japanese Patent Application No. 2023-543694 dated Oct. 9, 2025 with English machine translation; pp. 1-10.
Office Action issued for corresponding Japanese Patent Application No. 2023-543694 dated Sep. 9, 2025 with English machine translation; pp. 1-5.

* cited by examiner

PRIOR ART

CHARACTERISTICS MEASUREMENT DEVICE FOR OBJECT TO BE MEASURED AND CHARACTERISTICS MEASUREMENT METHOD FOR OBJECT TO BE MEASURED

BACKGROUND OF THE INVENTION

1. Field of the Invention

This disclosure relates to a characteristics measurement device for an object to be measured and a characteristics measurement method for an object to be measured.

2. Description of the Related Art

It is usually best to use electromagnetic waves of light or radio waves when measuring electrical, magnetic, or other characteristics of an object. However, it is difficult to measure the characteristics of objects such as human body, metals, or concrete blocks, which are difficult for light to penetrate. Therefore, we have developed a method to measure all kinds of objects, while taking advantage of the characteristics of the sound wave, which have high internal permeability to objects such as human body, metals, or concrete blocks, which are difficult for light to penetrate, and have a higher spatial resolution in the depth direction and in-plane direction of the object than radio waves of the same frequency because their wavelength is about five orders of magnitude shorter than that of electromagnetic waves of the same frequency. The apparatus and method for measuring the characteristics of an object by means of a sonic-induced electromagnetic field, which enables the object to be measured, are disclosed.

Patent Literature 1 discloses a technique for irradiating a sound wave to an object to be measured, measuring electromagnetic waves generated from the object to be measured, and measuring any of the electrical characteristics, magnetic characteristics, or electromagnetic/mechanical characteristics of the object to be measured from any of the intensity, phase, and frequency characteristics of the electromagnetic waves or a combination thereof. In addition, Patent Literature 2 discloses a technique for receiving an electromagnetic field generated by irradiating an amplitude-modulated sound wave to an object to be measured, and extracting at least one characteristic from an electrical characteristic, a magnetic characteristic, an electromechanical characteristic and a magnetomechanical characteristic of the object to be measured based on at least one measurement selected from a group consisting of the intensity, phase and frequency characteristics of the electromagnetic field.

Prior Art Literature

Patent Literature
Patent Literature 1: Japanese Pat. No. 4,919,967
Patent Literature 2: Japanese Pat. No. 5,892,623
Non-Patent Literature
Non-Patent Literature 1: E. Beaurepaire and 5 others, Appl. Phys. Lett., Vol.84, No.18, pp.3465-3467, 3 May 2004.

SUMMARY OF INVENTION

The technology disclosed in the above Patent Literature 1 is a method of reducing reverberation electromagnetic noise from a source of a sound wave, hereinafter referred to as "reverberation electromagnetic field caused by reverberation vibration associated with the transmission of a sound wave"

or simply "reverberation electromagnetic field". In order to avoid the "reverberation noise", also referred to as "reverberation noise" or "oscillator noise", there are restrictions on the distance between the source of a sound wave and an object to be measured, which impairs the degree of freedom of measurement and the signal sensitivity. The technology disclosed in the above Patent Literature 2 solves the problem in the technology disclosed in the above Patent Literature 1 that it takes time to measure the characteristics of an object to be measured, by irradiating an amplitude-modulated sound wave to the object to be measured, thereby reducing the measurement time of the characteristics of the object to be measured. However, the technology disclosed in the above Patent Literature 2 requires that the distance between the sound wave generator and the object to be measured be known in advance in order to shorten the measurement time of the characteristics of the object to be measured, thereby impairing the degree of freedom of measurement. In addition, in the above Patent Literature 2, the spatial resolution in the depth direction is lower than in the above Patent Literature 1, therefore the advantage in the measurement of the characteristics using a sound wave was lost.

The present invention was made in view of the above points and is intended to provide a characteristics measurement device for an object to be measured and a characteristics measurement method for an object to be measured, which can achieve at least one effect selected from (1) not to impair the degree of freedom in the measurement of characteristics using a sound wave, or in other words, to relax the restriction of the distance between the source of a sound wave and an object to be measured, (2) to receive the electromagnetic field that becomes the target signal by avoiding reverberating electromagnetic fields and (3) to shorten the measurement time of the characteristics of the object to be measured

Solution to Problem

In order to achieve the above mentioned purpose, a characteristics measurement device for an object to be measured according to the disclosure comprises; a sound wave generator that emits a sound wave; a receiver that receives from the object to be measured an electromagnetic field generated by the sound wave being irradiated to the object to be measured; a sound wave medium between the sound wave generator and the object to be measured the electromagnetic field separated from a reverberating electromagnetic field caused by reverberating vibrations of the sound wave generator in time; an inverse diffuser that inversely diffuses the electromagnetic field received by the receiver using a reference signal associated with the sound wave; and a measurement unit that extracts at least one characteristic selected from a group consisting of electrical characteristics, magnetic characteristics, electromechanical characteristics and magnetomechanical characteristics of the object to be measured based on at least one measurement selected from a group consisting of intensity, phase and frequency of the inversely diffused electromagnetic field.

Another characteristics measurement device for an object to be measured according to the disclosure comprises; a reference signal generator that generates a reference signal based on predetermined information; a sound wave generator that emits a sound wave generated based on the reference signal; a receiver that receives an electromagnetic field generated by the sound wave being irradiated to the object to be measured; an inverse diffuser that inversely diffuses the electromagnetic field received by the receiver using the reference signal; and a measurement unit that extracts at least one characteristic selected from a group consisting of electrical characteristics, magnetic characteristics, electromechanical characteristics and magnetomechanical characteristics of the object to be measured based on at least one measurement selected from a group consisting of intensity, phase and frequency of the inversely diffused electromagnetic field.

According to each characteristics measurement device for an object to be measured above, the time required to measure the characteristics can be reduced and the S/N ratio of the signal used to measure the characteristics can be improved. In addition, according to the characteristics measurement device for an object to be measured, the time required to measure the characteristics can be reduced and the restriction of the distance between the source of a sound wave and the object to be measured can be eliminated by suppressing the reverberating electromagnetic field caused by the transmission of the sound wave.

It is a suitable embodiment that each inverse diffuser above outputs a pulse compression signal or a correlation signal by correlating the above mentioned electromagnetic field received by the above mentioned receiver with the above mentioned reference signal. According to this embodiment of the characteristics measurement device for an object to be measured, the implementation can become easy, for example, by correlating with the reference signal and, furthermore, by using digital circuits and/or software. In addition, outputting a pulse compression signal, in other words, the fact that the electromagnetic field inversely diffused at each inverse diffuser above is a pulse compressed electromagnetic field, can further highlight the effect of improving the S/N ratio of the signal used for measuring the characteristics and reducing the time for measuring the characteristics.

Another suitable embodiment is that the above reference signal generator generates the above reference signal based on information having an impulsive autocorrelation characteristic as the above predetermined information or that the above sound wave generator generates the above sound wave based on information having an impulsive autocorrelation characteristic. According to this embodiment of the characteristics measurement device for an object to be measured, it is also possible to further eliminate the "noise" contained in the electromagnetic field received by the receiver, e.g., at least one noise selected from the group consisting of noise in the same frequency band as the oscillated sound wave, noise synchronized with the measurement unit, which includes reverberating electromagnetic fields accompanying the sound wave transmission, noise caused by external radio waves, noise caused by amplifiers and the like and thermal noise, and to improve the S/N ratio of the signal used to measure the characteristics. Another suitable embodiment is that the above information having the impulsive autocorrelation characteristics is M-sequence or that the above information having the impulsive autocorrelation characteristics is M-sequence. According to this embodiment of the characteristics measurement device for an object to be measured, it is easy to generate a reference signal by using M-sequence, which can be generated by a shift register, and the reference signal can be made longer without theoretical imitations, that is the S/N ratio can be made higher, by increasing the number of shift registers.

Another suitable embodiment is that the above reference signal generator generates the above reference signal based on information on which frequency varies continuously with time as the above predetermined information or that the above sound wave generator generates the above sound wave based on information on which frequency varies continuously with time. According to this embodiment of the characteristics measurement device for an object to be measured, furthermore, the frequency bandwidth of the reference signal can be freely set so that the reference signal can be shortened and the measurement can be processed at high speed.

Another suitable embodiment is that the above characteristics measurement device for an object to be measured further comprises a synchronous adder that synchronously adds the above electromagnetic field that has been inversely diffused a predetermined number of times and that the above measurement unit extracts the above characteristics of the object to be measured based on the above electromagnetic field synchronously added by the above synchronous adder. According to this embodiment of the characteristics measurement device for an object to be measured, it is further possible to obtain the desired S/N ratio by synchronous addition of the correlation signals.

Another suitable embodiment is that the above characteristics measurement device for an object to be measured is further provided with a subtractor that subtracts the signal obtained by inversely diffusing the electromagnetic field received at the above receiver from the inversely diffused electromagnetic field when the above object to be measured is not present. According to this embodiment of the characteristics measurement device for an object to be measured, it is further possible to eliminate the influence of time sidelobes that may be caused by inverse diffusion.

Another suitable embodiment is that the characteristics measurement device for an object to be measured is further provided with a phase detector that performs phase detection at the frequency of the above reference signal for the above electromagnetic field that has been inversely diffused. According to this embodiment of the characteristics measurement device for an object to be measured, the phase delay of the electromagnetic signal induced by the ultrasonic wave can be acquired by the phase detection and the characteristics of the object to be measured can be extracted from the phase delay.

Another suitable embodiment is that the above reference signal generator generates the above reference signal based on the complementary series as the predetermined information or that the above information having the impulsive autocorrelation characteristics is the complementary series. This embodiment of the characteristics measurement device for an object to be measured can further eliminate the effect of time sidelobes that may be caused by inverse diffusion.

In order to achieve the above mentioned purpose, a characteristics measurement method for an object to be measured according to the disclosure comprises; a sound wave emission process for emitting a sound wave from a sound wave generator; a receiving process for delaying the electromagnetic field from the object to be measured, which is generated by the irradiation of the sound wave to the object to be measured, using the sound wave medium between the sound wave generator and the object to be measured and receiving the delayed electromagnetic field; an inverse diffusion process for inversely diffusing the received electromagnetic field using a reference signal associated with the sound wave; and a measurement process for extracting at least one characteristic selected from a group consisting of electrical, magnetic, electromechanical, and magnetomechanical characteristics of the object to be measured based on at least one measurement selected from a group consisting of the intensity, phase, and frequency of the inversely diffused electromagnetic field wherein the electromagnetic field is separated from a reverberating electromagnetic field caused by reverberating vibration of the sound wave generator in time.

Another characteristics measurement method for an object to be measured according to the disclosure generates a reference signal based on predetermined information; emits a sound wave generated based on the reference signal; receives an electromagnetic field generated by the sound wave being irradiated to the object to be measured; inversely diffuses the received electromagnetic field using the reference signal; and extracts at least one characteristic selected from a group consisting of electrical characteristics, magnetic characteristics, electromechanical characteristics and magnetomechanical characteristics of the object to be measured based on at least one measurement selected from a group consisting of intensity, phase and frequency of the inversely diffused electromagnetic field.

According to the above characteristics measurement methods for an object to be measured, the time required to measure the characteristics can be reduced and the S/N ratio of the signal used to measure the characteristics can be improved. In addition, according to the above characteristics measurement methods for an object to be measured, the time required to measure the characteristics can be reduced and the restriction of the distance between the source of a sound wave and the object to be measured can be eliminated by suppressing the reverberating electromagnetic field caused by the transmission of the sound wave.

In the present application, the reverberating electromagnetic field caused by the reverberating vibration of the source generating the sound wave is not limited to the reverberating electromagnetic field caused by the fundamental frequency and harmonics of the source. For example at least the following reverberation electromagnetic fields (a) to (c) at the source, which are different from the fundamental frequency and the n-th harmonic, can also be included in the "reverberation electromagnetic field" in this application when an ultrasonic transducer is used as the source, (a) Reverberating electromagnetic fields due to frequencies generated by radial vibration modes;

(b) Reverberating electromagnetic field due to the frequency generated by the thickness-shear vibration mode (c) Reverberating electromagnetic fields due to frequencies generated by interference due to multiple reflections in the probe.

Therefore, it is important that the reduction of the reverberant electromagnetic field can be realized with a high degree of accuracy by using a characteristics measurement device for an object to be measured according to the disclosure, another characteristics measurement device for an object to be measured according to the disclosure, a characteristics measurement method for an object to be measured according to the disclosure or another characteristics measurement method for an object to be measured according to the disclosure even when a reverberating electromagnetic field due to the frequencies generated by the various modes as described above is generated.

According to a characteristics measurement device for an object to be measured according to the disclosure and a characteristics measurement method for an object to be measured according to the disclosure, the time required to measure the characteristics can be reduced and the S/N ratio of the signal used to measure the characteristics can be improved. In addition, according to the characteristics measurement device for an object to be measured according to the disclosure and the characteristics measurement method for an object to be measured according to the disclosure, the time required to measure the characteristics can be reduced and the restriction of the distance between the source of a sound wave and the object to be measured can be eliminated by suppressing the reverberating electromagnetic field of the source of a sound wave.

DETAILED DESCRIPTION OF THE INVENTION

Figure 1:
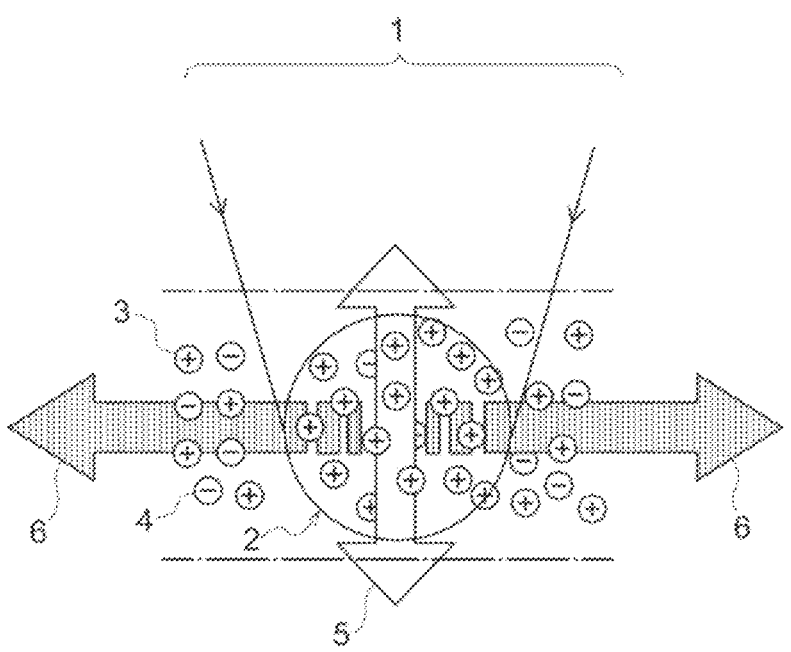
FIG. 1 shows an electromagnetic field induced by a sound wave irradiating a portion of an object to be measured.

Examples of embodiments of the present disclosure will be described below with reference to drawings. In each drawing, identical or equivalent components and parts are given the same reference numbers. Dimensional proportions in the drawings may differ from the actual proportions because they may be exaggerated for the sake of explanation.

First, an electromagnetic field induced in the area where a sound wave is irradiated when an object to be measured is irradiated by a sound wave is explained. Details of the electromagnetic field induced in the area where the sound wave is irradiated are disclosed in the above Patent Literature 1.

FIG. 1 illustrates an electromagnetic field induced by a sound wave irradiating the area to be measured. In FIG. 1, the sound wave focusing beam 1 is focused on the area 2 of the object to be measured. The circled + and − symbols indicate the positively charged particles 3 and the negatively charged particles 4, respectively. In the sound wave focusing area 2 of the object to be measured, the concentration of the positively charged particles 3 and the negatively charged particles 4 is out of balance, indicating the state of charge distribution in which the positively charged particles 3 outnumber the negatively charged particles 4. Arrow 5 indicates the direction of sound vibration of the sound wave focusing beam 1, which corresponds to the direction of the electric field. Arrow 6 shows the magnetic field generated in the plane perpendicular to arrow 5.

As shown in FIG. 1, the irradiation of the sonic focused beam 1 causes the positively charged particles 3 and the negatively charged particles 4 to vibrate in the sound vibration direction, i.e., in the direction of the arrow indicated by the sign 5, at the frequency of the sound wave. The vibration of the positively charged particles 3 and the negatively charged particles 4 then induces a magnetic field in the direction of the arrow indicated by the sign 6 that is generated in the plane perpendicular to the vibration direction 5 because the charges are vibrating. No electromagnetic field is induced because the electromagnetic fields generated are out of phase with each other by $\pi$ and they cancel each other out. However, in the sound wave focusing area 2 of the object to be measured, there are more the positively charged particles 3 than the negatively charged particles 4 in the charge distribution state, therefore they cannot completely cancel each other out and a net electromagnetic field, arrow 6, is induced. Consequently, if the electromagnetic field induced by the sound wave is observed and a change in the intensity of the electromagnetic field is observed, it indicates that a change has occurred in the charge distribution, i.e., a change in the concentration of the positively charged particles 3 or the negatively charged particles 4, or both. As a result, from the measurement of the electromagnetic field induced by the sound wave, it is possible to measure the characteristic value of the charged particles in the object to be measured, in this case the change in their concentration.

FIG. 1 shows an example of measuring changes in the concentration of charged particles from the measurement of the electromagnetic field induced by a sound wave, however changes in the characteristic values of the charged particles that can be measured include not only changes in concentration, but also those in mass, size, shape, number of charges, or interaction force with the medium surrounding the charged particles. For example, from some other knowledge of the state of the object to be measured, or from knowledge by some other means, if changes in concentration, mass, size, shape, and charge number are not possible, changes in the intensity of the measured electromagnetic field can be linked to changes in the interaction force with the medium surrounding the charged particles. Thus, for example, the intensity change of the measured electromagnetic field can be linked to a change in the electron or positive ion polarization rate.

In each embodiment and variant of the present disclosure described below, the electric field, dielectric constant, electric field or spatial gradient of dielectric constant can be measured as an electrical property of the object to be measured. In each embodiment and variant of the present disclosure described below, the magnetization due to electron spin or nuclear spin can also be measured as the magnetic property of the object to be measured. Specifically, as in the case of electric polarization, an electromagnetic field is generated when the magnetization varies with time; according to Maxwell's equation, the radiated electric field is proportional to the second derivative of the magnetization with respect to time, see Non-Patent Literature 1. Therefore, it is possible to measure the magnitude and direction of the magnetization from the electromagnetic field intensity and phase.

In each embodiment and variant of the present disclosure described below, acoustic magnetic resonance due to electron spins or nuclear spins can be measured as a magnetic property of the object to be measured. Specifically, it is expected that at a certain resonance frequency, a sound wave is efficiently absorbed and the direction of electron spins or nuclear spins changes, resulting in a significant change in electromagnetic field intensity and phase at that frequency. The resonance frequency can be determined as information. In addition, as in ordinary ESR, electron spin resonance, and NMR, nuclear magnetic resonance, scanning the frequency of the sound wave will provide a spectrum and information on the electron spins and the nuclear spins. In addition, a relaxation time of the electron spins and the nuclear spins can be measured.

In each embodiment and variant of the present disclosure described below, piezoelectric properties or magnetostrictive properties can be measured as electromechanical properties or magnetomechanical properties of the object to be measured as follows. In principle, ionic crystals without inversion symmetry produce electric polarization due to strain. Therefore, the magnitude of the polarization can be obtained from the intensity of the electromagnetic field to be measured, which can be called the sound wave induced electromagnetic field. By scanning the sound wave, the piezoelectric properties of the object to be measured can be imaged. Furthermore, from the direction of sound wave propagation and the angular distribution of the electromagnetic field generated, the piezoelectric tensor can be measured contactlessly without electrodes on the object to be measured.

In each embodiment and variant of the present disclosure described below, the magnetostriction property can be measured as an electromechanical property or magnetomechanical property of the object to be measured as follows. Magnetostriction is a phenomenon in which electron orbitals are changed due to crystal distortion and a change is applied to the electron spin magnetization through orbital-spin interactions. In other cases, the magnetic domain structure is changed by external strain, resulting in a change in the effective magnetization in a macroscopic region, about the size of a sonic beam spot. Crystal distortion can also cause changes in the crystal field splitting, which can alter the electronic state and change the magnitude of the electron spin magnetization. These temporal changes are thought to generate electromagnetic fields. Therefore, the magnitude of magnetization, orbital-spin interaction, sensitivity in crystal distortion and electron orbital change, sensitivity in crystal field splitting and distortion, relationship between crystal field splitting and electron spin state or relationship between magnetic domain structure and distortion can be determined from the intensity of the sound wave induced electromagnetic field. The magnetostriction tensor can be measured in a non-contact manner without electrodes on the object to be measured from the direction of sound wave propagation and radiation intensity. Imaging of the magnetostrictive properties as well as the piezoelectric properties is possible.

In each embodiment and variant of the present disclosure described below, a sound wave is irradiated to the object to be measured and the electromagnetic field generated by this object is measured. In each embodiment and variant of the present disclosure, the electromagnetic field is separated from the reverberating electromagnetic field caused by the reverberating vibration of the sound wave generator in time by a method of measuring the characteristics of the object to be measured including the following processes (i) through (iv), (i) a sound wave emission process for emitting a sound wave from a sound wave generator;

(ii) a receiving process for delaying the electromagnetic field from the object to be measured, which is generated by the irradiation of the sound wave to the object to be measured, using the sound wave medium between the sound wave generator and the object to be measured and receiving the delayed electromagnetic field;

(iii) an inverse diffusion process for inversely diffusing the received electromagnetic field using a reference signal associated with the sound wave; and (iv) a measurement process for extracting at least one characteristic selected from a group consisting of electrical, magnetic, electromechanical, and magnetomechanical characteristics of the object to be measured based on at least one measurement selected from a group consisting of the intensity, phase, and frequency of the inversely diffused electromagnetic field.

Viewed from another perspective, in each embodiment and variant of the present disclosure, a sound wave generated based on a reference signal generated based on predetermined information is irradiated to the object to be measured, the electromagnetic field generated by the irradiation to the object to be measured is received, and the received electromagnetic field is inversely diffused using the above reference signal. More precisely, the received electromagnetic field is correlated with the above reference signal to generate a correlation signal. Based on at least one measurement selected from a group consisting of the intensity, phase, and frequency of the correlation signal, at least one characteristic selected from a group consisting of the electrical, magnetic, electromechanical, and magnetomechanical characteristics of the object to be measured can then be extracted. The electrical property of the object to be measured is a change in at least one characteristic value selected from a group consisting of the electric field, dielectric constant, spatial gradient of the electric field or dielectric constant, concentration, mass, size, shape, number of charges, and interaction of the charged particles with the medium surrounding the charged particles in the object to be measured. The magnetic property of the object to be measured is the magnetization due to the electron spin or nuclear spin of the object to be measured, or the acoustic magnetic resonance due to the electron spin or nuclear spin of the object to be measured. The electromechanical and magnetomechanical properties of the object to be measured are the piezoelectric properties or magnetostrictive properties of the object to be measured.

The First Embodiment

Figure 2A:
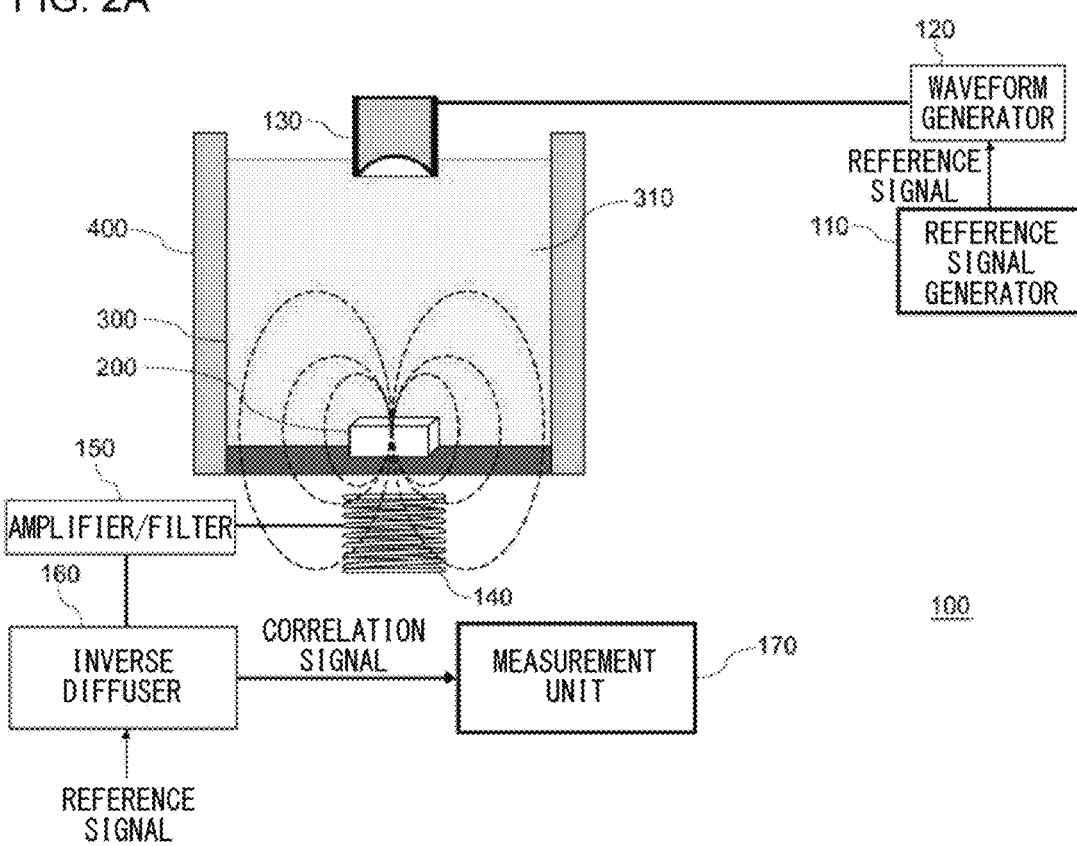
FIG. 2A and 2B show an example configuration of a characteristic measurement device according to the first embodiment of the present disclosure.
Figure 2B:
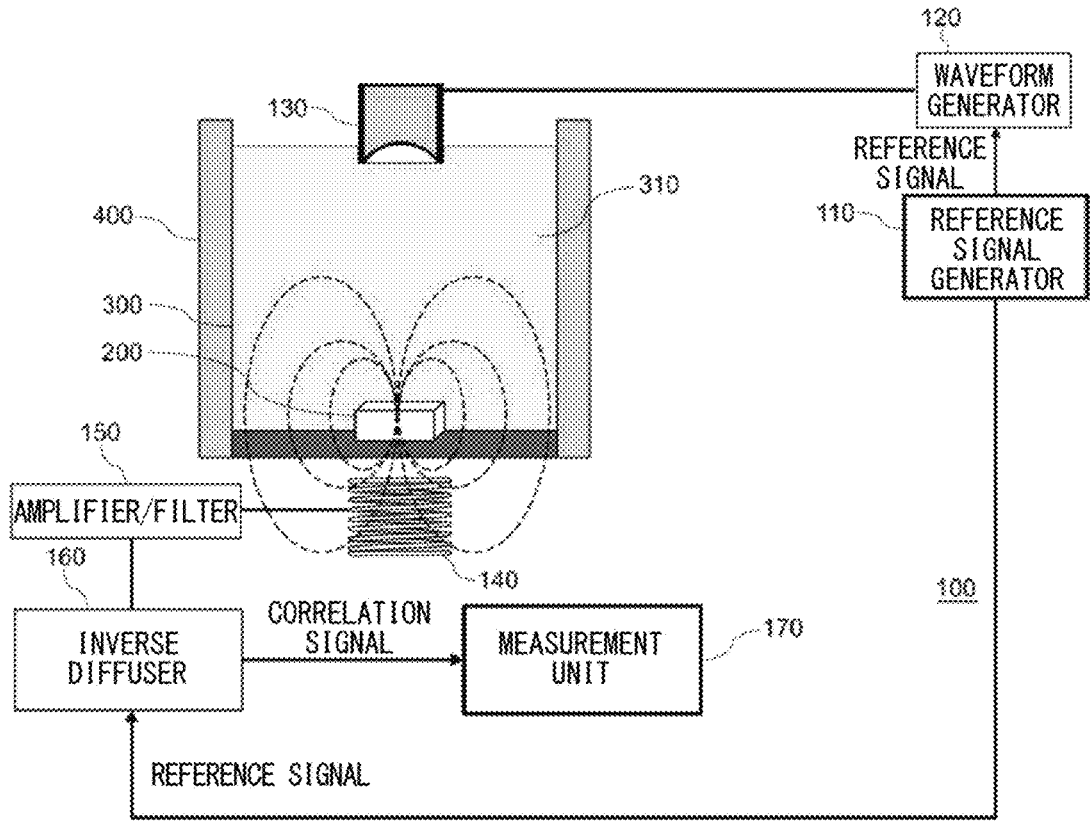

FIG. 2 shows an example configuration of a characteristics measurement device 100. In FIG. 2A, the source and path of the "reference signal" are simplified to make the drawing easier to read. However, as described below, the reference signal is shown in FIG. 2B as a more detailed drawing because it is used not only as a signal that serves as the basis for the waveform generated by a waveform generator 120, but also as a signal used for inverse diffusion of the electromagnetic field in the inverse diffuser 160. The same applies to FIG. 10, FIG. 11, FIG. 12, and FIG. 13. As shown in FIG. 2, the characteristics measurement device 100 comprises a reference signal generator 110, a waveform generator 120, a sound wave generator 130, a receiver 140, an amplifier/filter 150, an inverse diffuser 160, and a measurement unit 170. The characteristics measurement device 100 shown in FIG. 2 is a device for measuring the characteristics of an object 200 to be measured. In this embodiment, a ferrite magnet, which is an example of a ferromagnetic material, is used as the object 200 to be measured.

The reference signal generator 110 generates a reference signal that is the basis for the waveform generated by the waveform generator 120. The reference signal generated by the reference signal generator 110 is not only the signal that serves as the basis of the waveform generated by the waveform generator 120, but also the signal used for inverse diffusion of the electromagnetic field in the inverse diffuser 160 described below. The inverse diffuser 160 can pulse compress the electromagnetic field by inversely diffusing the electromagnetic field using the reference signal.

In this embodiment, the reference signal generator 110 generates a reference signal based on information with impulsive or sharp autocorrelation characteristics, specifically M-sequences, as the basis for the reference signal. An impulse is a pulse with infinitesimal temporal width and infinite height. In this embodiment, the reference signal generator 110 may also generate a reference signal based on information on which frequency varies continuously with time as the basis for the reference signal. Such a reference signal is a chirp signal on which frequency varies continuously with time. The reference signal generator 110 may also generate a reference signal based on a complementary series as the information on which the reference signal is based.

It is easy to generate a reference signal when using M-sequence as the information on which the reference signal is based because M-sequence can be generated with shift registers, and the reference signal can be made longer without theoretical limitations by increasing the number of shift registers. Lengthening the reference signal leads to a higher S/N ratio of the electromagnetic field.

The frequency bandwidth of the reference signal can be freely set and the measurement can be faster than with M-sequence when a chirp signal is used as the basis of the reference signal. The S/N ratio of pulse compression is proportional to the product of the signal length and the frequency bandwidth of the reference signal. The bandwidth of the reference signal is an integer multiple of the center frequency when M-sequence is used. Therefore, it is necessary to lengthen the signal in order to increase the S/N ratio of the electromagnetic field. On the other hand, the bandwidth of the reference signal can be wider, i.e., the reference signal can be shorter, than when the M-sequence is used and the measurement of the characteristics of the object 200 to be measured can be faster when a chirp signal is used as the information on which the reference signal is based.

The reference signal generator 110 may also generate a reference signal based on Golay codes, Barker codes, etc., as the information on which the reference signal is based.

The reason for generating the reference signal will now be explained. The most important point to note in the characteristics measurement device 100 as shown in FIG. 2 is that the oscillator noise, synonymous with reverberating electromagnetic field in this embodiment, from the sound wave generator 130 which generates ultrasonic waves is to be avoided. Obviously, this oscillator noise cannot be escaped even with narrow band detection because it is in the same frequency band as the target signal. The oscillator noise is expected to be much more powerful than the signal received at the receiver 140. For example, the target signal will be buried in the oscillator noise as shown in FIG. 8B and the target signal cannot be obtained if the sound wave generator 130 and the object 200 to be measured are placed in close contact as shown in FIG. 8A.

Figures 8A, 8B, 9A, 9B:
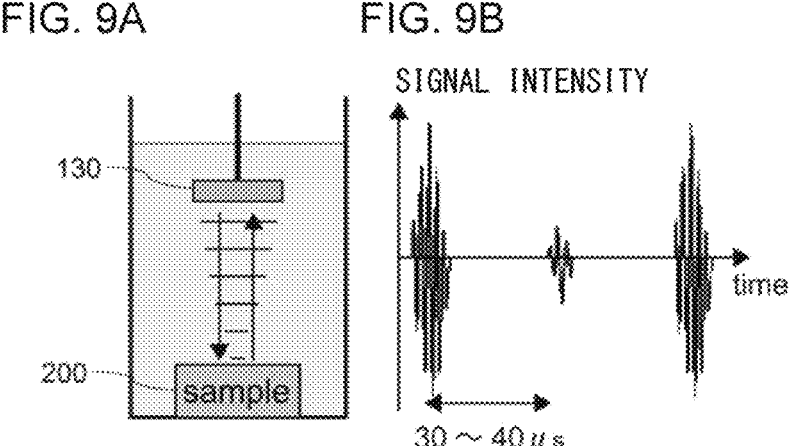
FIG. 8A and 8B show a configuration where a sound wave generator and an object to be measured are in close contact.
FIG. 9A and 9B show a configuration where a sound wave generator and an object to be measured are separated from each other.

The oscillator noise and the target signal from the object 200 to be measured that is received at the receiver 140 can be separated in time as shown in FIG. 9B by separating the sound wave generator 130 from the object 200 to be measured as shown in FIG. 9A and using the time it takes for the sound wave to reach the object 200 to be measured from the sound wave generator 130. For example, there is a delay of 40 μs (microseconds) for a sound wave to propagate 60 mm (millimeters) because the speed of sound in water is 1500 m (meters)/s (seconds). On the other hand, the propagation time of electromagnetic waves is negligibly short compared to the propagation time of sound wave. Therefore, the ultrasonic oscillator noise and the target signal from the object 200 to be measured can be separated in time as shown in FIG. 9B by providing a sound wave medium between the sound wave generator 130 and the object 200 to be measured and using the pulse method with ultrasonic excitation pulses that are sufficiently shorter than the sound wave propagation time.

However, the pulse method generally has a very short effective integration time compared to the measurement time. For example, the time width of the signal generated by the reception of the sound wave by the object 200 to be measured is less than 10 μs, whereas the repetition time of ultrasonic pulses is typically 0.1 s, i.e., 100 Hz. Therefore, the effective signal integration time is only 0.01% of the measurement time. In other words, the signal-to-noise, S/N, ratio obtained by integrating for one second is small. In many cases, a clear signal cannot be obtained without a long measurement time. This is a major obstacle in practical use.

Therefore, the characteristics measurement device 100 of this embodiment generates a sound wave from the sound wave generator 130 based on a reference signal, receives the electromagnetic field generated by the object 200 to be measured at the receiver 140, and inversely diffuses the received electromagnetic field using the reference signal on which the sound wave is based. The characteristics measurement device 100 independently compresses the oscillator noise and the target signal from the object 200 to be measured which is received at the receiver 140 by inversely diffusing the electromagnetic field received at the receiver 140 using the reference signal on which the sound wave is based and can obtain the target signal from the object 200 to be measured.

The waveform generator 120 generates a waveform based on the reference signal generated by the reference signal generator 110. In the following description, waveform generator 120 generates waveforms based on reference signal generated based on M-sequences. M(12,11,9,5,3,1) is used as the M-sequence. The waveform generator 120 generates a 0.5 MHz square wave modulated signal in the M-sequence M(12,11,9,5,3,1).

Figure 3:
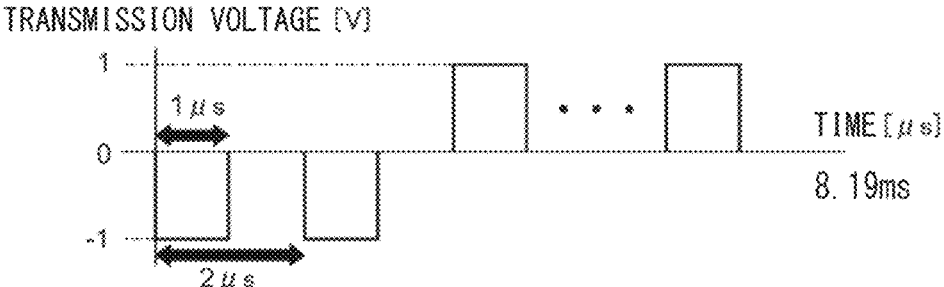
FIG. 3 shows an example of a signal generated by a waveform generator.

The sound wave generator 130 generates a sound wave based on the signal generated by the waveform generator 120. The sound wave generator 130 is an example of sound wave generators of this disclosure. For example, an ultrasonic transducer that vibrates based on the signal generated by the waveform generator 120 is used for the sound wave generator 130. The sound wave generator 130 may be an array-type probe used in ultrasonic diagnostic equipment. FIG. 3 shows an example of a signal generated by the waveform generator 120. The modulation frequency is the resonance frequency $f_0$ of the sound wave generator 130. The spatial resolution in the direction of ultrasonic wave propagation and the ultrasonic beam spot size are determined by this resonance frequency. The code sequence used has its impulsive autocorrelation characteristics, in other words, its autocorrelation function is sharp enough. Such a code sequence includes M series belonging to the PN code. In this embodiment, a sound wave is generated based on a 0.5 MHz (megahertz) square wave modulated signal in the M-sequence M (12,11,9,5,3,1). The duration of sound wave generation in a single measurement is 8.19 ms (milliseconds).

In this example, the sound wave generator 130, which serves as a sound wave transmitter or sound wave generator, transmits a sound wave toward the object 200 to be measured, sound wave transmitting process. The object 200 to be measured is installed at the bottom of the tank 300. The sound wave generator 130 is placed in water 310, corresponding to the sound wave medium, filled in the tank 300 so that the distance from the object 200 to be measured is 130 mm. The tank 300 is surrounded by an electromagnetic shield 400 that blocks the electromagnetic field from the outside so that the electromagnetic field generated by the object 200 to be measured can be accurately detected.

The receiver 140 detects, also referred to as "receives", the electromagnetic field generated, i.e., radiated, by the object 200 to be measured, the receiving process. The receiver 140 may be any device capable of detecting electromagnetic fields. For example, various antennas such as loop, electrostatically coupled or array antennas, sensors that detect electric charge, electric field or magnetic field or array sensors may be used as the receiver 140. Here, in the receiving process of this embodiment, the electromagnetic field generated by the sound wave from the object 200 is received with a delay. Because water 310, which serves as a sound wave medium, is provided between the sound wave generator 130 and the object 200 to be measured, thereby delaying the time for the sound wave transmitted from the sound wave generator 130 to reach the object 200 to be measured.

The amplifier/filter 150 amplifies and filters the electromagnetic field detected at the receiver 140. In this embodiment, the amplifier/filter 150 amplifies the electromagnetic field detected at the receiver 140 by a predetermined amount and passes it through a bandpass filter to remove bands outside the predetermined frequency band. The predetermined frequency band is, for example, 9.9 MHz to 10.1 MHz.

The inverse diffuser 160 performs inverse diffusion of the electromagnetic field amplified and filtered by the amplifier/filter 150 using the reference signal generated by the reference signal generator 110, more specifically, the reference signal related to the sound wave, inverse diffusion process. The aforementioned reference signal related to the sound wave also means a reference signal that diffuses the sound wave or a voltage signal that excites the diffused sound wave.

Specifically, the inverse diffuser 160 outputs either a correlation signal generated by correlating an electromagnetic field detected, i.e., received, at the receiver 140 and amplified and filtered by the amplifier/filter 150 with a reference signal generated by the reference signal generator 110, or a pulse compression signal generated by correlating the electromagnetic field with the reference signal. The electromagnetic field can be pulse compressed or pulse compress processed by the inverse diffuser 160 performing inverse diffusion of the electromagnetic field including the target signal using the reference signal correlated to the sound wave. The electromagnetic field generated by the object 200 to be measured can be separated from the oscillator noise generated by the sound wave generator 130 in the measurement process described below and the electromagnetic field generated by object 200 can be clearly confirmed by pulse compressing the electromagnetic field, i.e., by outputting the correlated signal or the pulse compression signal by the inverse diffuser 160. In other words, the electromagnetic field that becomes the target signal, electromagnetic field from the object 200, can be separated from the reverberant electromagnetic field in time while the duration of the reverberant electromagnetic field caused by the reverberant vibration of the sound wave generator 130 is shortened. As a result, according to the characteristics measurement device 100 and the characteristic measurement method of this embodiment, the effect of the reverberating electromagnetic field of the sound wave generator 130 can be significantly reduced, the resolution of the electromagnetic field from the object 200 to be measured as the target signal can be improved, and the measurement time can be significantly reduced, in other words, measurement can be made faster compared to conventional technologies.

Figure 4:
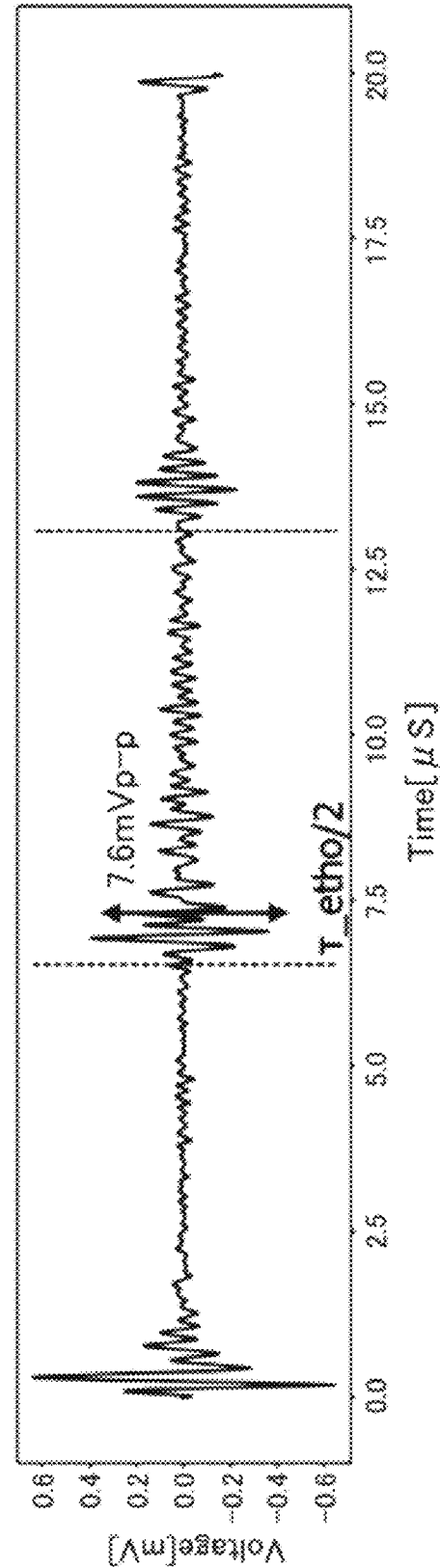
FIG. 4 shows an example of an electromagnetic field inversely diffused by the inverse diffuser.

FIG. 4 is a graph showing an example of the electromagnetic field inversely diffused by the inverse diffuser 160. The measurement time is 10 ms, which is close to the generation time of the sound wave. The waveforms generated from 0 μs in the graph in FIG. 4 are based on the oscillator noise generated by the sound wave generator 130, while the waveforms generated from about 6.5 μs are based on the electromagnetic field generated by the object 200 and inversely diffused by the inverse diffuser 160. Thus, the characteristics measurement device 100 of this embodiment can clearly confirm the electromagnetic field generated by the object 200 to be measured by inversely diffusing the electromagnetic field using the inverse diffuser 160.

Figure 5:
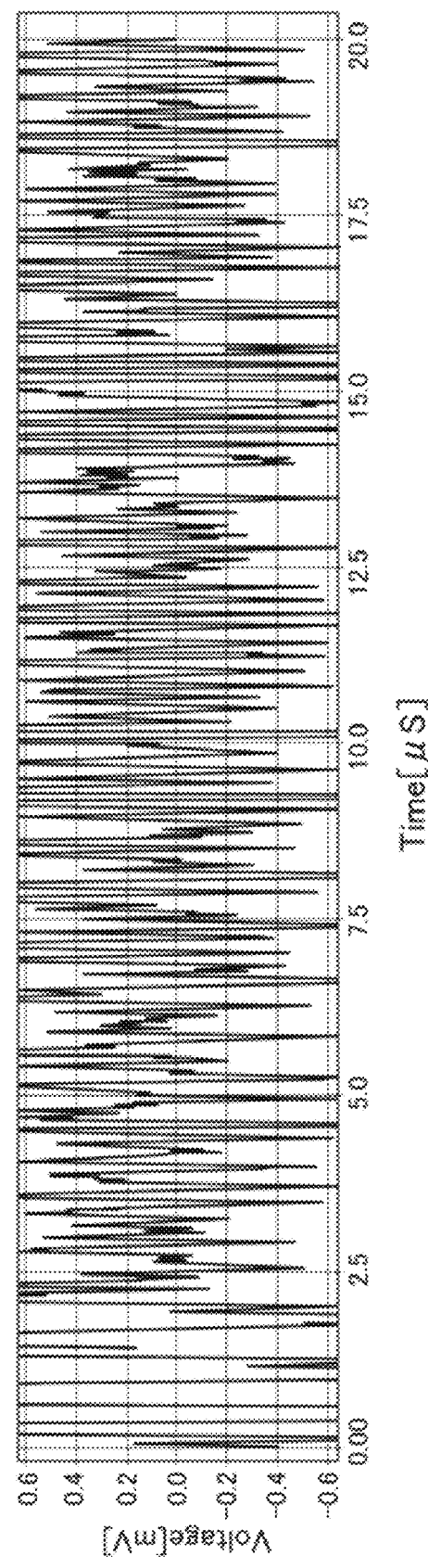
FIG. 5 shows an example of 5 integrations without inverse diffusion, using pulsed ultrasound instead of M-sequence.

As a comparative example, the case in which pulsed ultrasonic is used instead of M-sequence and the electromagnetic field is integrated without inversely diffusing it. FIG. 5 shows an example of an electromagnetic field that was integrated 5 times using pulsed ultrasonic instead of M-sequence. It takes 10 ms for the entire measurement when the measurement time per measurement is 2 ms. As shown in the graph in FIG. 5, in five integrations, the electromagnetic field is buried in the oscillator noise, making it impossible to observe. Therefore, by inversely diffusing the electromagnetic field using the inverse diffuser 160, the characteristics measurement device 100 can significantly improve the S/N ratio over the same measurement time compared to integrating the electromagnetic field without inversely diffusing it using pulsed ultrasonic.

Figure 6:
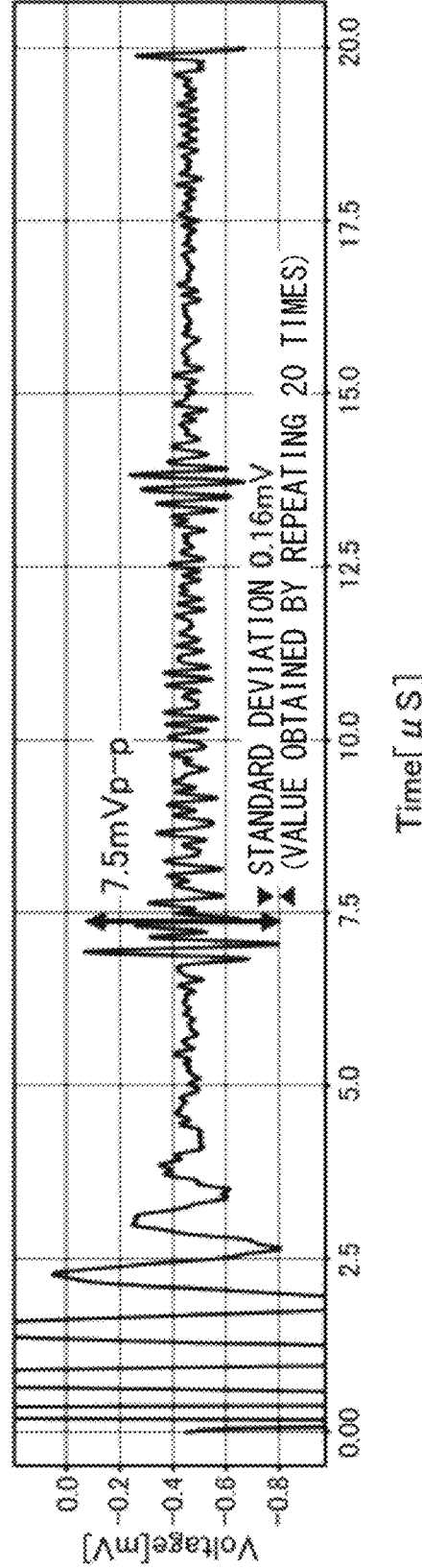
FIG. 6 shows an example of 5,000 integrations without inverse diffusion, using pulsed ultrasound instead of M-sequence.

As another comparative example, the case in which pulsed ultrasonic is used instead of M-sequence and the electromagnetic field is integrated a sufficient number of times without inversely diffusing it. FIG. 6 shows an example of an electromagnetic field that was integrated 5000 times using pulsed ultrasonic instead of M-sequence. It takes 10 seconds to obtain the graph shown in FIG. 6 when the measurement time per measurement is 2 ms. Therefore, by inversely diffusing the electromagnetic field using the inverse diffuser 160, the characteristics measurement device 100 of this embodiment can greatly reduce the measurement time compared to integrating the electromagnetic field without inversely diffusing it.

In a measurement example using the characteristics measurement device 100 of this embodiment and employing a ferrite magnet as the object 200 to be measured, a measurement example has been confirmed in which sufficient resolution was achieved even in a short time of about $\frac{1}{1000}$ compared to the case where the electromagnetic field is not inversely diffused using the inverse diffuser 160. The inventors understand that, in this example, this is the effect of improved resolution because it is possible that the 0.5 MHz transducer employed as the sound wave generator 130 had a reverberating electromagnetic field caused by the "radial vibration mode", "thickness-shear vibration mode" or "interference due to multiple reflections in the probe" or a combination of these, as already mentioned.

The measurement unit 170 extracts the characteristics of the object 200 to be measured based on the electromagnetic field inversely diffused by the inverse diffuser 160, measurement process. Specifically, the measurement unit 170 extracts at least one characteristic selected from a group consisting of electrical characteristics, magnetic characteristics, electromechanical characteristics, and magnetomechanical characteristics of the object 200 to be measured based on at least one measurement selected from a group consisting of the intensity, phase, and frequency of the electromagnetic field inversely diffused by the inverse diffuser 160 to Extraction.

Specifically, as described above, the measurement unit 170 shortens the duration of the reverberating electromagnetic field caused by the reverberating vibration of the sound wave generator 130, and then, with the electromagnetic field that becomes the target signal separated in time from the reverberating electromagnetic field, can measure the electric field, the dielectric constant or the spatial gradient of the electric field or the dielectric constant as the electrical characteristics of the object 200 to be measured in an extremely short time compared to conventional techniques. The measurement unit 170 can also measure acoustic magnetic resonance caused by electron spins or nuclear spins as magnetic properties of the object 200 to be measured. The measurement unit 170 can also measure piezoelectric or magnetostrictive properties as electromechanical or magnetomechanical properties as magnetic properties of the object 200 to be measured. The measurement unit 170 can also measure magnetostrictive properties as electromechanical or magneto-mechanical properties of the object 200 to be measured.

Figure 7:
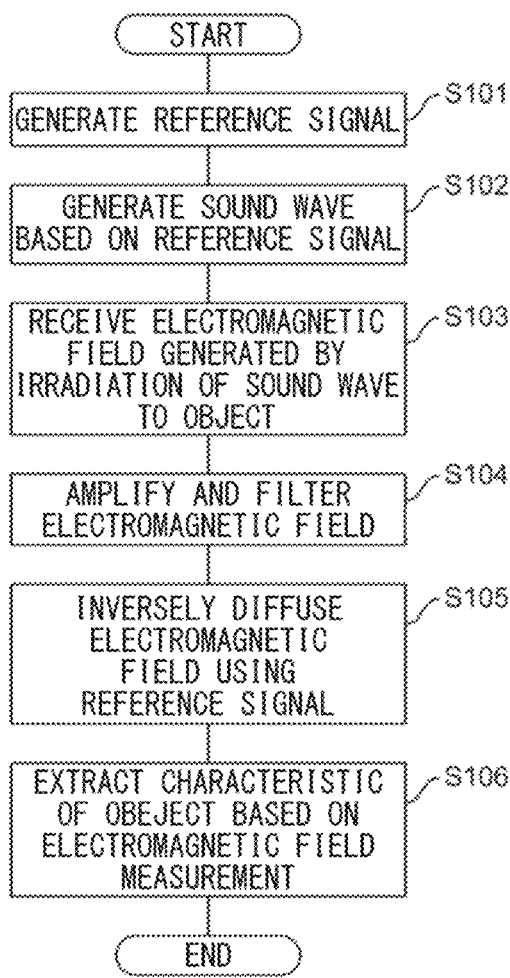
FIG. 7 is a flow diagram of a characteristic measurement process by a characteristic measurement device.

Next, the operation of the characteristics measurement device 100 will be described. FIG. 7 is a flowchart showing the flow of the characteristic measurement process by the characteristics measurement device 100. The characteristic measurement process by the characteristics measurement device 100 is performed by the CPU, Central Processing Unit, of the computer connected to the characteristics measurement device 100, which reads the computer program, expands it in RAM, i.e., Random Access Memory, executes it and controls each part of the characteristics measurement device 100.

The characteristics measurement device 100 generates a predetermined reference signal at the reference signal generator 110 in step S101. In this embodiment, the characteristics measurement device 100 generates a reference signal based on information having an impulsive autocorrelation characteristic, specifically M-sequence, as described above. In this embodiment, the characteristics measurement device 100 also generates a reference signal based on information on which frequency varies continuously with time. Such a reference signal is a chirp signal on which frequency varies continuously with time.

After generating the reference signal in step S101, the characteristics measurement device 100 subsequently generates a waveform based on the reference signal in step S102 and generates a sound wave at the sound wave generator 130 based on the generated waveform.

After generating the sound wave at the sound wave generator 130 in step S102, the characteristics measurement device 100 subsequently receives at the receiver 140, in step S103, the electromagnetic field emitted by the object 200 to be measured due to reception of the sound wave generated by the sound wave generator 130.

Once the electromagnetic field is received by the receiver 140 in step S103, the characteristics measurement device 100 subsequently amplifies and filters the electromagnetic field received by the receiver 140 in step S104 with the amplifier/filter 150. Specifically, the characteristics measurement device 100 amplifies the electromagnetic field received by the receiver 140 by a predetermined amount and passes it through a bandpass filter to remove bands other than the predetermined frequency band. The predetermined frequency band is, for example, 9.9 MHz to 10.1 MHz.

After amplifying and filtering the electromagnetic field in step S104, the characteristics measurement device 100 then in step S105 inversely diffuses the filtered electromagnetic field using the reference signal at the inverse diffuser 160. For example, the inverse diffuser 160 correlates the filtered electromagnetic field with the reference signal and outputs a correlation signal.

After inversely diffusing the electromagnetic field in step S105, the characteristics measurement device 100 subsequently extracts the characteristics of the object 200 to be measured in step S106, based on the measurement of the inversely diffused electromagnetic field, at the measurement unit 170. Specifically, the measurement unit 170 extracts at least one characteristic selected from a group consisting of electrical, magnetic, electromechanical, and magnetomechanical characteristics of the object 200 to be measured based on at least one measurement selected from a group consisting of the intensity, phase, and frequency of the inversely diffused electromagnetic field.

The characteristics measurement device 100 of this embodiment can separate the electromagnetic field generated by the object 200 to be measured from the oscillator noise generated by the sound wave generator 130 and can clearly confirm the electromagnetic field generated by the object 200 to be measured, by executing the series of processes shown in FIG. 7. In addition, the characteristics measurement device 100 can greatly reduce the measurement time by inversely diffusing the electromagnetic field at the inverse diffuser 160 by executing the series of processes shown in FIG. 7, compared to the case where the electromagnetic field is integrated without inverse diffusion.

In the above embodiment, the characteristics of the object 200 to be measured are extracted by measuring the electromagnetic field inversely diffused at the inverse diffuser 160 in the measurement unit 170, however the invention is not limited to the above example.

Example 1 of a Variant of the First Embodiment

Figure 10:
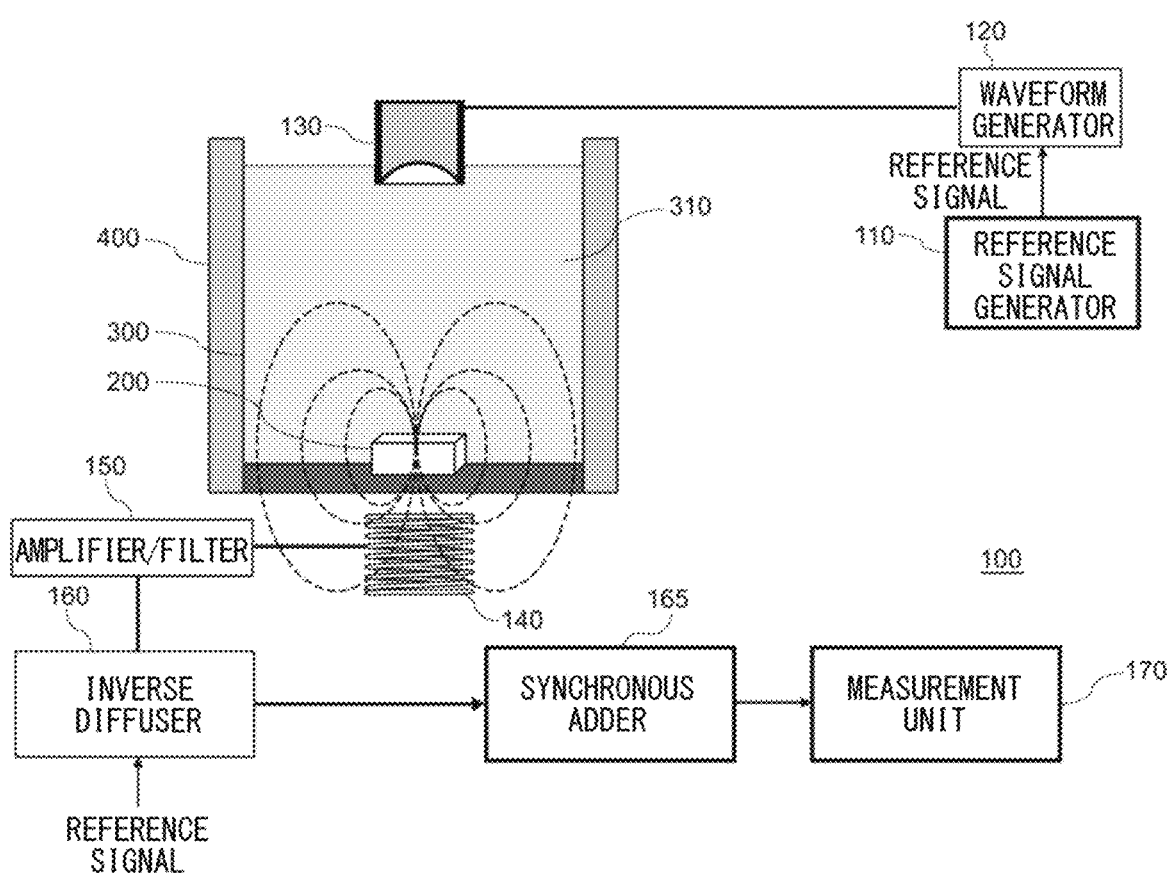
FIG. 10 shows a characteristic measurement device according to variant 1 of the first embodiment of the present disclosure.

FIG. 10 shows a variant of the characteristics measurement device 100 of the embodiment of the disclosure described above. The characteristics measurement device 100 shown in FIG. 10 has the same configuration as shown in FIG. 2 except for the following point. That is a synchronous adder 165 is added to synchronously add the electromagnetic field inversely diffused by the inverse diffuser 160 a predetermined number of times.

As in this variant, in a measurement method where the magnitude of the electromagnetic field generated by the object 200 to be measured is assumed to be small, the signal-to-noise ratio may be limited by the implementation limitations of the reference signal length, reference signal bandwidth and reception bandwidth, which determine the S/N ratio. Even in such cases, it becomes possible to accelerate the measurement while meeting the S/N ratio required for the measurement by synchronously adding a predetermined number of times the electromagnetic field inversely diffused by the inverse diffuser 160.

A sidelobe is generated in the inversely diffused signal when the electromagnetic field is inversely diffused using a reference signal, as in this variant. This is called a time sidelobe and is assumed to affect the discrimination of the electromagnetic field generated by the object 200 to be measured.

Example 2 of a Variant of the First Embodiment

Figure 11:
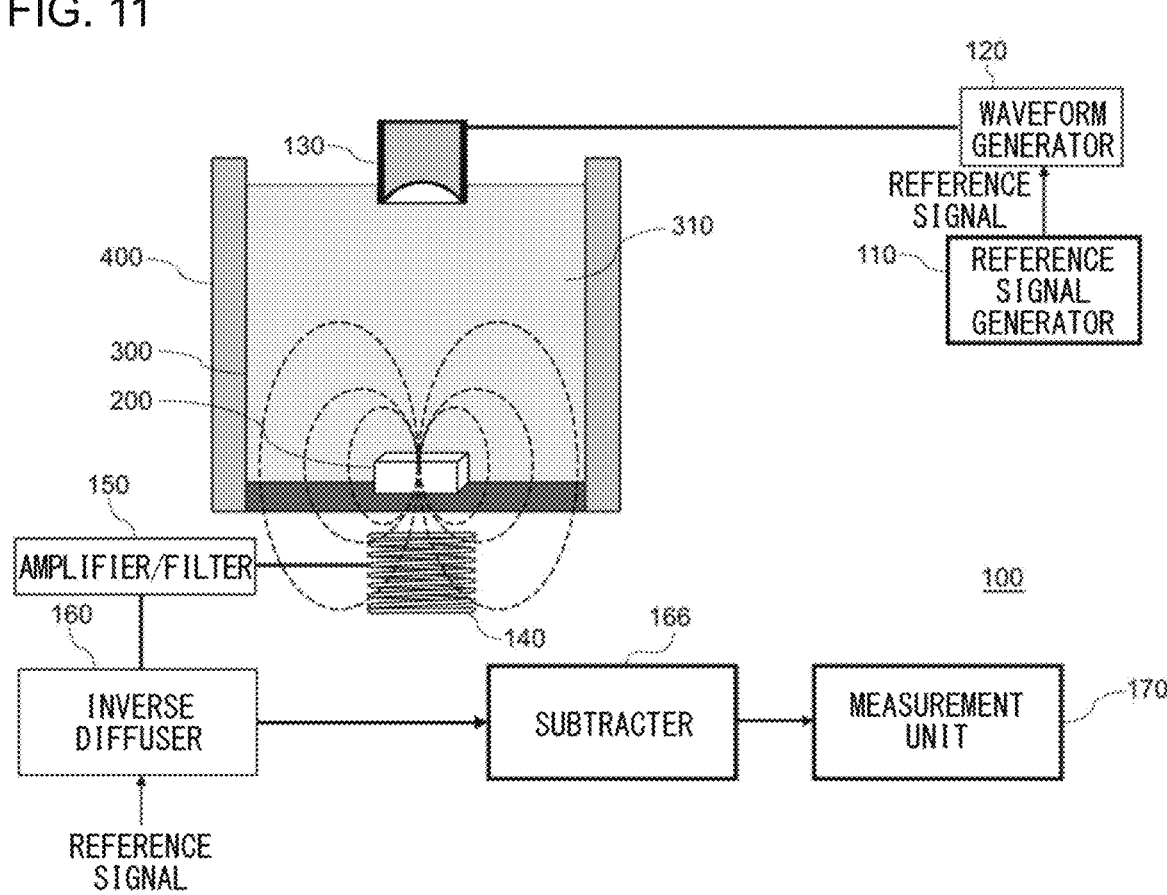
FIG. 11 shows a characteristic measurement device according to variant 2 of the first embodiment of the present disclosure.

FIG. 11 shows a variant of the characteristics measurement device 100 of the embodiment of the disclosure described above. The characteristics measurement device 100 shown in FIG. 11 has the same configuration as shown in FIG. 2 except for the following point. That is a subtracter 166 is added to subtract the signal obtained by inversely diffusing the electromagnetic field received when the object 200 to be measured is not present by the receiver 140 from the electromagnetic field received when the object 200 to be measured is present by the receiver 140 and inversely diffused by the inverse diffuser 160. The signal can be stored, for example, in a memory of a computer connected to the characteristics measurement device 100. The subtracter 166 can reduce the time sidelobe by subtracting the signal from the electromagnetic field inversely diffused by the inverse diffuser 160.

As in this variant, in a measurement method where the magnitude of the electromagnetic field generated by the object 200 to be measured is assumed to be small, the discrimination of the electromagnetic field generated by the object 200 to be measured can be improved by removing time sidelobes of the oscillator noise that are always present by the subtracter 166. The characteristics measurement device 100 can also eliminate the effect of time sidelobes that may be caused by inverse diffusion by using a reference signal generated by the reference signal generator 110 based on a complementary series.

Example 3 of a Variant of the First Embodiment

Figure 12:
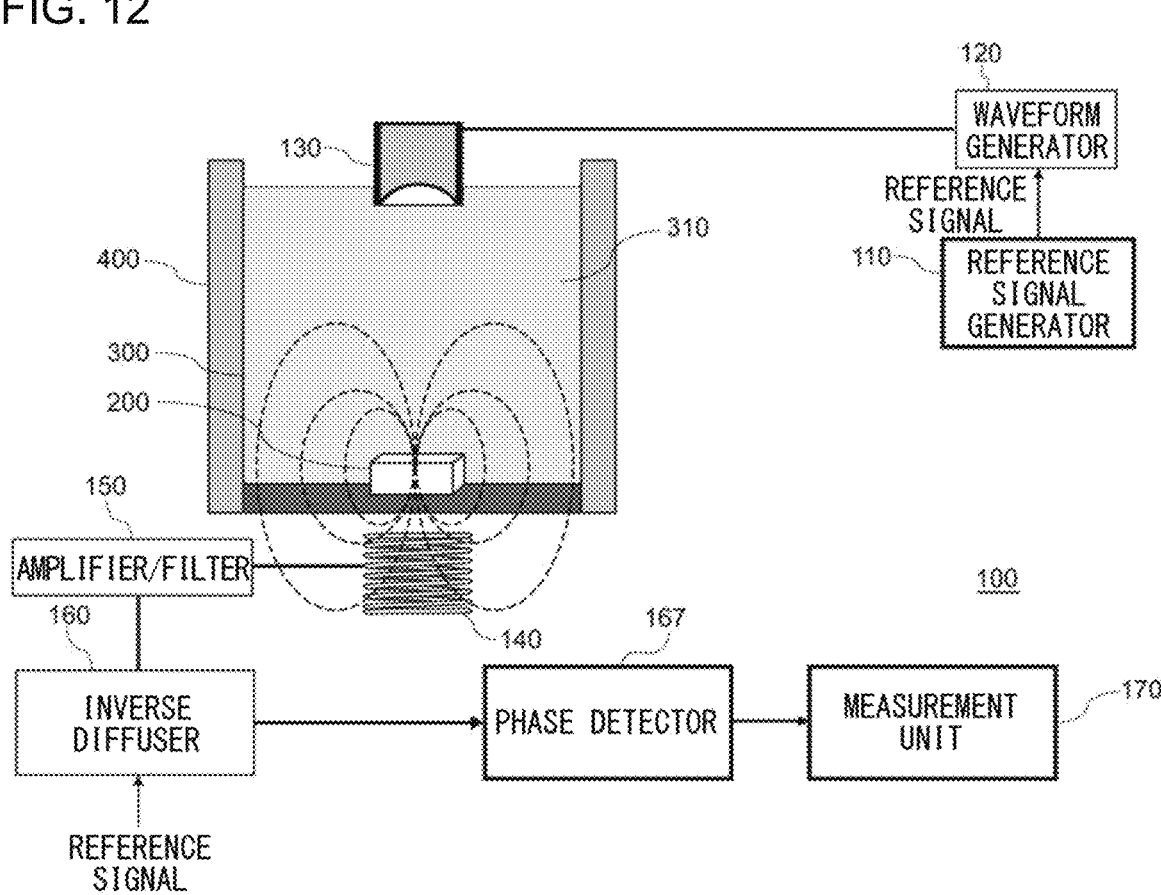
FIG. 12 shows a characteristic measurement device according to variant 3 of the first embodiment of the present disclosure.

FIG. 12 shows a variant of the characteristics measurement device 100 of the embodiment of the disclosure described above. The characteristics measurement device 100 shown in FIG. 12 has the same configuration as shown in FIG. 2 except for the following point. That is a phase detector 167 is added to perform phase detection at the frequency of the reference signal for the electromagnetic field inversely diffused by the inverse diffuser 160.

The voltage of the electromagnetic field inversely diffused by the inverse diffuser 160 is proportional to the piezoelectric or piezomagnetic coefficient. The measurement method used in this variant is to obtain the piezoelectric coefficient in the case of a dielectric material and the electromagnetic coefficient in the case of a magnetic material. The characteristics measurement device 100 can acquire both the real and imaginary parts of the generalized complex piezoelectric coefficient or the complex piezomagnetic coefficient by performing phase detection in the phase detector 167. The real part is the normal piezoelectric or piezomagnetic coefficient that is synchronized with the excited sound wave and the imaginary part characterizes the energy loss of the piezoelectric and piezomagnetic phenomena in the frequency band of the excited sound wave. Therefore, the characteristics measurement device 100 can evaluate factors related to energy loss with respect to electrical, magnetic, electromechanical and magnetomechanical characteristics of the object 200 to be measured from the imaginary part by performing phase detection at the phase detector 167. Furthermore, the characteristics measurement device 100 can further improve the S/N ratio compared to the case where no phase detection is performed, by performing phase detection at the phase detector 167.

Example 4 of a Variant of the First Embodiment

Figure 13:
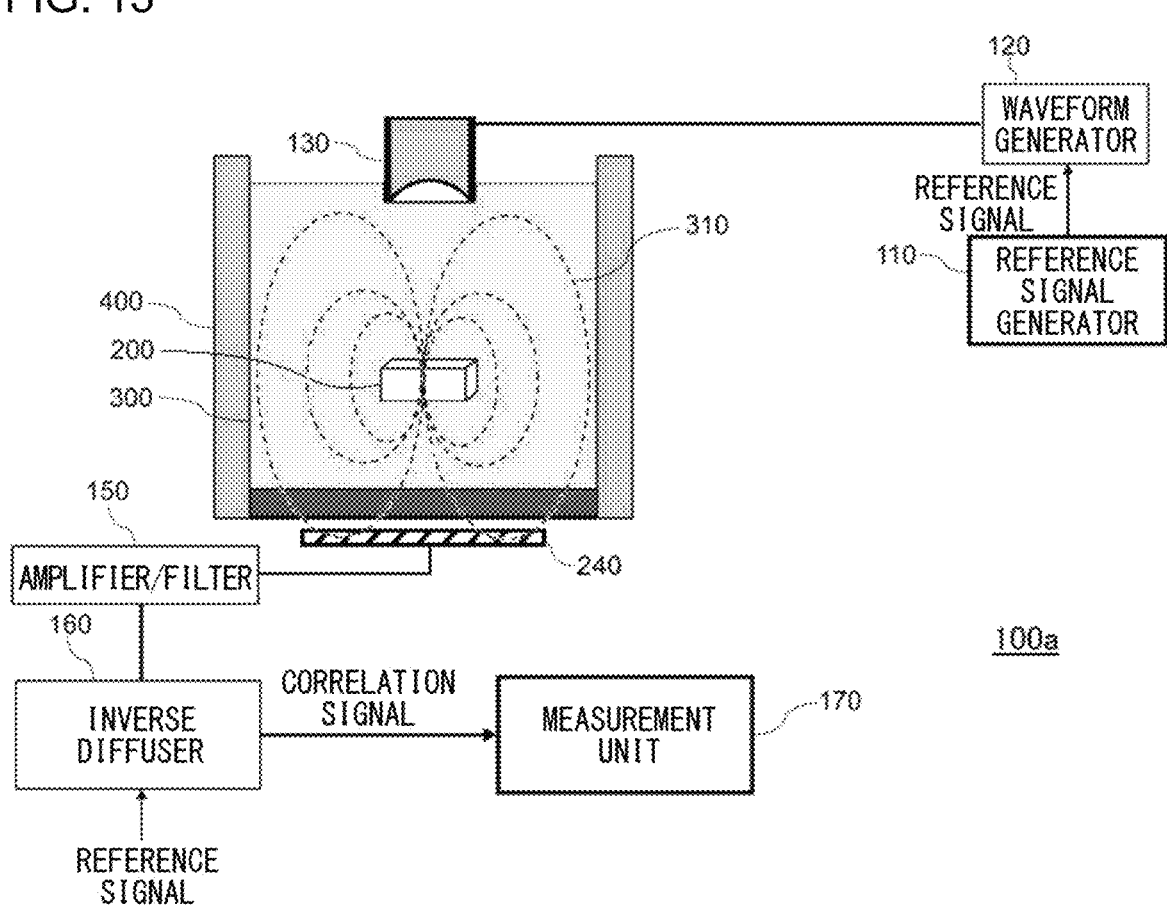
FIG. 13 shows a characteristic measurement device according to variant 4 of the first embodiment.

FIG. 13 shows the characteristics measurement device 100a according to this variant. The characteristics measurement device 100a shown in FIG. 13 has the same configuration as shown in FIG. 2 except for the following point. That is the coil-type antenna is changed to a metal plate, a copper plate in this variant, that plays the role of an electrostatic coupling antenna. Thus, as shown in FIG. 13, the characteristics measurement device 100a in this variation comprises a reference signal generator 110, a waveform generator 120, a sound wave generator 130, a receiver 240, an amplifier/filter 150, an inverse diffuser 160 and a measurement unit 170. In FIG. 13, a retainer for holding the object 200 to be measured is not shown.

In this variant example, a bovine Achilles tendon, which is an example of a dielectric material, is used as the object 200 to be measured. Accordingly, in this variant example, the receiver 240 detects, i.e., receives, the electromagnetic field, the electric field in particular, generated by the sound wave emitted from the sound wave generator 130, thereby the characteristics of the object 200 being measured. In this variant, the synchronous addition process of the electromagnetic field with pulse compression, one of the inverse diffusion processes, is performed 12 times, 5 ms×12 times in detail, and the measurement time is 60 ms.

Figure 14:
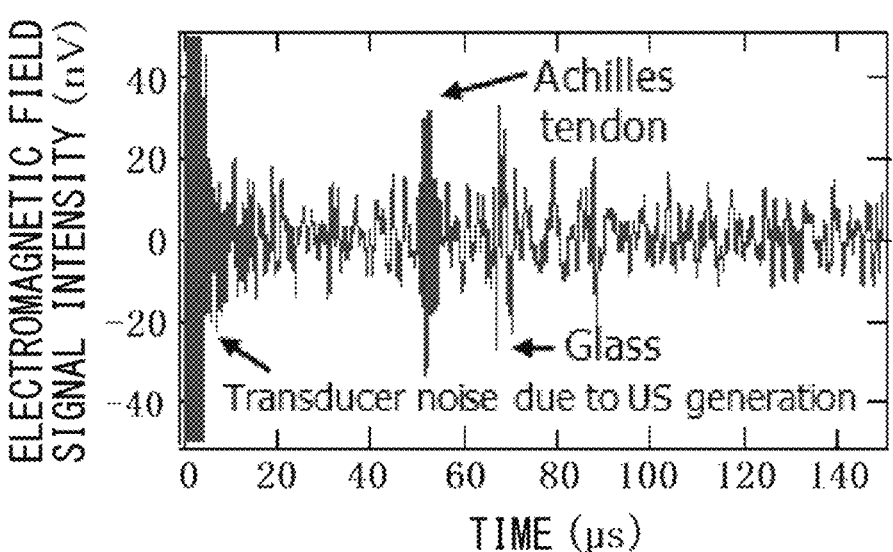
FIG. 14 shows a results of measurement of an object to be measured when using a characteristic measurement device according to variant 4 of the first embodiment.
Figure 15:
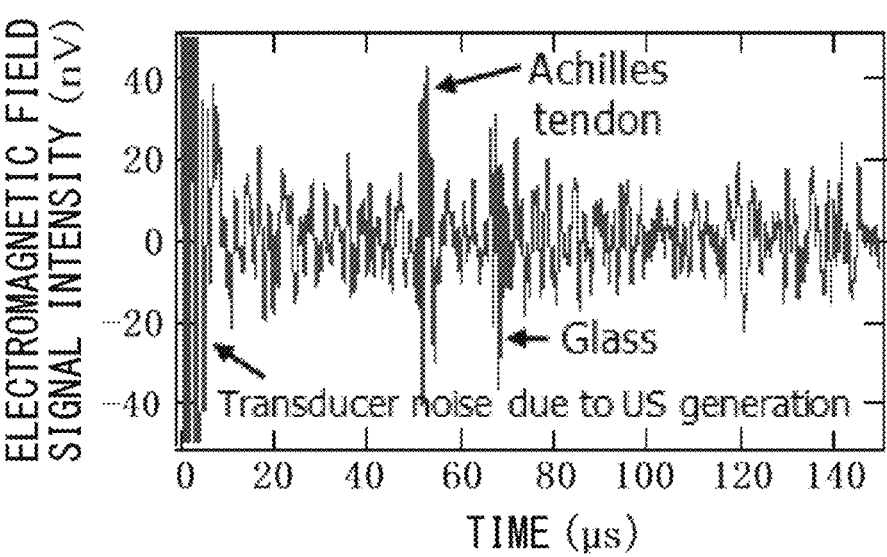
FIG. 15 shows a results of measurement of an object to be measured when using a comparative example.

FIG. 14 shows the measurement results of the objects 200 to be measured when the characteristics measurement device 100a for this variant is used. FIG. 15 shows the measurement results of the objects 200 to be measured when the comparative example is used. Here, the comparative example shown in FIG. 15 is identical to the measurement conditions of this variant, except that the electromagnetic field that serves as the target signal is not inversely diffused, the synchronous addition process was performed 5000 times, and the measurement time was 50 s (seconds). The vertical axis in each drawing is the electromagnetic field signal strength (nV) and the horizontal axis is the time (μs).

As shown in FIG. 14, in this variant, it can be seen that the electromagnetic field signal from the object 200 to be measured is clearly shown to the extent that it is sufficiently distinguishable from the reverberating electromagnetic field described above. It can also be seen that the electromagnetic field signal from the object 200 to be measured shown in FIG. 14 is separated from the reverberating electromagnetic field in time and that the reverberating electromagnetic field associated with the sound wave emission is suppressed. Therefore, it can be seen that the result shown in FIG. 14 is superior to the detection accuracy of the electromagnetic field signal from the object 200 to be measured shown in FIG. 15. Furthermore, from the viewpoint of achieving a faster measurement, it is worth noting time that the measurement time, 60 ms, in this variant is about $\frac{1}{830}$ of the measurement time, 50 s, in the comparative example.

Figure 16:
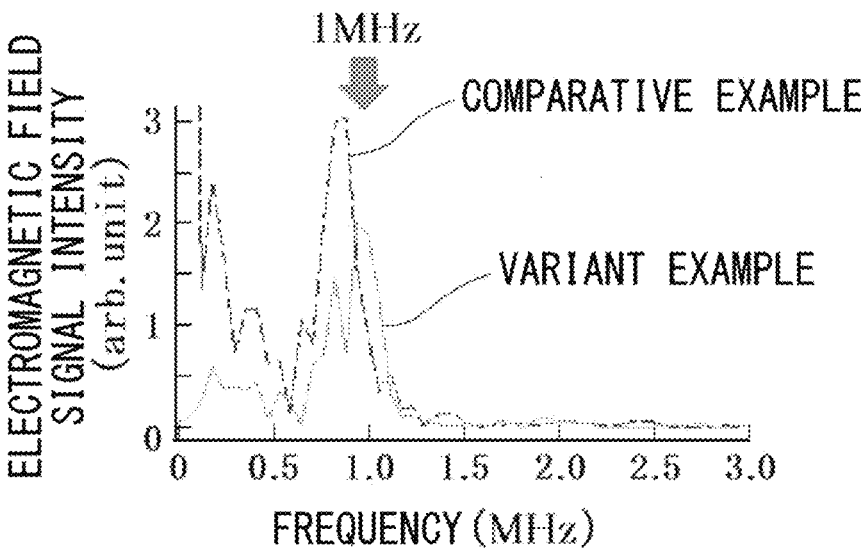
FIG. 16 is a diagram for comparing a frequency spectrum of the reverberation electromagnetic field corresponding to this variant, solid line (thinner line), and the comparative example, dotted line, in order to compare the intensity of the reverberation electromagnetic field in a low frequency range.

FIG. 16 is also a diagram for comparing the frequency spectra of the reverberating electromagnetic field in the low frequency range corresponding to this variant (solid line, i.e., thinner line) and the comparative example (dotted line), from 0 to 17 μs, in order to compare the intensity of the reverberating electromagnetic field in the low frequency range. As FIG. 16 shows that the reverberating electromagnetic field of this variant (solid line) with a low frequency component different from the frequency, 1 MHz, of the sound wave generator 130 is significantly reduced, compared to the corresponding reverberating electromagnetic field of the comparative example (dotted line).

As shown in FIG. 16, the frequency spectrum of the reverberating electromagnetic field from the sound wave generator 130 can be significantly reduced compared to the conventional technology, by employing the characteristics measurement device 100a and the characteristic measurement method of this variant example. As a result, the electromagnetic field that becomes the target signal, i.e., electromagnetic field from the object 200 to be measured, can be separated from the reverberating electromagnetic field in time while reducing the duration of the reverberating electromagnetic field caused by the reverberating vibration of the sound wave generator 130.

In this variant, as in the case where the characteristics measurement device 100 is employed, the effect of the reverberating electromagnetic field of the sound wave generator 130 can be significantly reduced, the resolution of the electromagnetic field from the object 200 to be measured as the target signal can be improved and the measurement time can be significantly reduced compared to conventional technology.

In this variant, in terms of separating the electromagnetic field signal from the reverberating electromagnetic field in time, suppressing the reverberating electromagnetic field associated with the transmission of the sound wave and improving the S/N ratio, it is easy to achieve more accurately at least one of the following (A) to (D) using synchronous addition of the inversely diffused can measure than using electromagnetic field with a long diffuse signal length.

(A) To separate the electromagnetic field signal from the object 200 to be measured, which is the target signal, from the reverberating electromagnetic field in time;

(B) To suppress the reverberating electromagnetic field associated with the wave emission;

(C) To improve the S/N ratio; and (D) To significantly shorten the measurement time.

Other Embodiments

A reference signal generator 110 is arranged in each embodiment or variant described above, however each embodiment or variant described above does not necessarily require a reference signal generator 110. For example, FIG. 17 shows a characteristics measurement device 100b according to other variant of embodiments of the disclosure.

Figure 17:
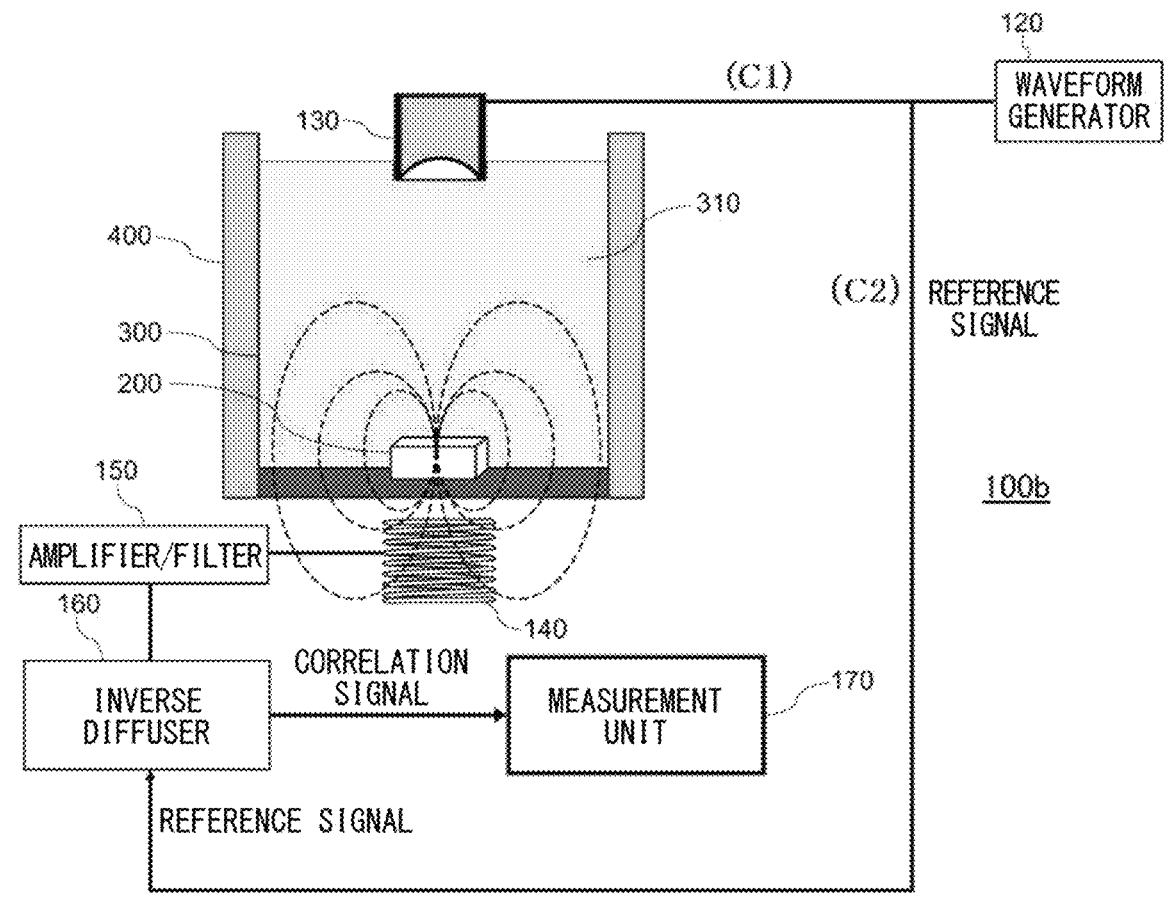
FIG. 17 shows a characteristic measurement device for another variant of the first embodiment.

In the embodiment shown in FIG. 17, the reference signal can be directly transmitted from the waveform generator 120. In other words, the waveform generator 120 can serve as the reference signal generator 110 in the first embodiment.

Specifically, the reference signal generated in advance by the waveform generator 120 is transmitted to the inverse diffuser 160 via cable C2. As a result, the reference signal is used as the signal used for inverse diffusion of the electromagnetic field at the inverse diffuser 160, as in the embodiment or each variation described above.

Also in this variant, as in the case of using the characteristics measurement device 100 of the first embodiment, it is possible to shorten the duration of the reverberating electromagnetic field caused by the reverberating vibration of the sound wave generator 130 and then to separate the electromagnetic field that becomes the target signal, i.e., the electromagnetic field from the object 200 to be measured, from the reverberating electromagnetic field in time. As a result, according to the characteristics measurement device 100 and the characteristics measurement method of this embodiment, the influence of the reverberating electromagnetic field of the sound wave generator 130 can be significantly reduced, the resolution of the electromagnetic field from the object 200 to be measured, which is the target signal, can be improved and the measurement time can be significantly shortened compared to conventional technology.

Water is employed as the sonic medium in each of the embodiments and variations described above, however the sonic medium is not limited to water. For example, liquids other than water, e.g., various aqueous solutions, alcohols, liquid oils, gases including air, resins or metals can also be employed as sonic media for adjusting sound velocity, as long as the effects of each embodiment or each variation are not substantially lost.

The characteristics measurement apparatus and method for measuring the characteristics of the object to be measured of each embodiment and each variation can nondestructively measure at least one characteristic selected from a group consisting of electrical characteristics, magnetic characteristics, electromechanical characteristics, and magnetomechanical characteristics of the object to be measured. Therefore, they can be used for objects or structures containing colloidal solutions, liquid crystals, solid electrolytes, ionic crystals, semiconductors, dielectrics, metals, magnetic materials, magnetic fluids or any of these composite materials or for measurement techniques of various characteristics including measurement techniques in biotechnology field for functional devices, and the like.

The embodiments of the disclosure have been described in detail above with reference to the accompanying drawings, however the technical scope of the invention is not limited to each embodiment or each variation described above. For example, even if there is no electromagnetic shield, at least a part of the effects of each embodiment and each variant described above can be achieved. It is obvious that a person skilled in the art can conceive of various changes or modifications within the scope of the technical concept described in the claims, and these changes or modifications should be understood to be within the technical scope of the invention.

In each embodiment and each variation described above, it is also possible to employ various processors other than the CPU to execute the characteristics measurement process that was executed by the CPU by reading the software or program. In this case, the processor may be PLD, i.e., Programmable Logic Device, such as FPGA, i.e., Field-Programmable Gate Array, on which circuit configuration can be changed after manufacturing or may be a dedicated electric circuits such as ASIC, i.e., Application-Specific Integrated Circuit, which is a processor with a circuit configuration designed specifically to execute a particular process. The characteristics measurement process may be executed by one of these various processors or by a combination of two or more processors of the same or different types, e.g., multiple FPGAs, and combinations of CPUs and FPGAs. The hardware structure of these various processors is more specifically an electrical circuit that combines circuit elements such as semiconductor devices, etc.

In each embodiment and variation described above, a program for the characteristic measurement process may be pre-stored, i.e., installed, in ROM or storage as a possible embodiment that can be employed, however each embodiment and variation described above are not limited to such aspects. The program may be provided in a form recorded on a non-transitory recording medium such as CD-ROM, i.e., Compact Disk Read Only Memory, DVD-ROM, i.e., Digital Versatile Disk Read Only Memory and USB, i.e., Universal Serial Bus, memory, etc. The program may also be downloaded from an external device via a network.

Industrial Applicability

The characteristics measurement device for an object to be measured and the characteristics measurement method for an object to be measured may be widely used in various technical fields, including various industrial, chemical, power and energy, material, medical, pharmaceutical and life science fields.

Reference Signs List

100, 100a, 101b Characteristics measurement device
110 Reference signal generator
120 Waveform generator
130 Sound wave generator
140, 240 Receiver
150 Amplifier/filter
160 Inverse diffuser
170 Measurement unit
200 Object to be measured
300 Tank
310 Water
400 Electromagnetic shield

What is claimed is:

1. A characteristics measurement device for an object to be measured, comprising:
   a reference signal generator that generates a reference signal based on predetermined information;
   a sound wave generator that emits a sound wave generated based on the reference signal;
   a receiver that receives an electromagnetic field generated by the sound wave being irradiated to the object to be measured;
   an inverse diffuser that inversely diffuses the electromagnetic field received by the receiver using the reference signal;
   a synchronous adder that adds synchronously the electromagnetic field inversely diffused a predetermined number of times, and
   a measurement unit that extracts at least one characteristic selected from a group consisting of electrical characteristics, magnetic characteristics, electromechanical characteristics and magnetomechanical characteristics of the object to be measured based on at least one measurement selected from a group consisting of intensity, phase and frequency of the inversely diffused electromagnetic field added by the synchronous adder.

2. The characteristics measurement device according to claim 1, wherein the inverse diffuser outputs a pulse compression signal by correlating the electromagnetic field received by the receiver with the reference signal.

3. The characteristics measurement device according to claim 1, wherein the sound wave generator generates a sound wave based on information having an impulsive auto-correlation characteristic and wherein the information having the impulsive autocorrelation characteristics is M-sequence or a complementary sequence.

4. The characteristics measurement device according to claim 1, wherein the sound wave generator generates a sound wave based on information on which frequency varies continuously with time.

5. The characteristics measurement device according to claim 1, further comprising a subtractor that subtracts the signal obtained by inversely diffusing the electromagnetic field received at the receiver from the inversely diffused electromagnetic field when the object to be measured is not present.

6. The characteristics measurement device according to claim 1, further comprising a phase detector that detect a phase of the electromagnetic field inversely diffused.

7. A characteristics measurement method for an object to be measured, comprising;

generating a reference signal based on predetermined information;

emitting a sound wave generated based on the reference signal;

receiving an electromagnetic field generated by the sound wave being irradiated to the object to be measured;

inversely diffusing the received electromagnetic field using the reference signal;

adding synchronously the electromagnetic field inversely diffused a predetermined number of times, and extracting at least one characteristic selected from a group consisting of electrical characteristics, magnetic characteristics and characteristics, electromechanical magnetomechanical characteristics of the object to be measured based on at least one measurement selected from a group consisting of intensity, phase and frequency of the inversely diffused electromagnetic field added by the synchronous adder.

8. The characteristics measurement method for an object to be measured according to claim 7, further comprising subtracting step of subtracting the signal obtained by inversely diffusing the electromagnetic field received at the receiver from the inversely diffused electromagnetic field when the object to be measured is not present.

9. The characteristics measurement method for an object to be measured according to claim 7, further comprising a phase detecting step of detecting a phase of the electromagnetic field inversely diffused.

\* \* \* \* \*